United States Patent
Tholakanahalli et al.

(10) Patent No.: US 10,661,080 B2
(45) Date of Patent: May 26, 2020

(54) SHAPED EPICARDIAL LEAD AND PLACEMENT SYSTEM AND METHOD

(71) Applicant: Kobara Medical Inc., Eden Prairie, MN (US)

(72) Inventors: Venkatakrishna N. Tholakanahalli, Minnetonka, MN (US); Andy C. Pfahnl, Eden Prairie, MN (US); John J. Allen, Mendota Heights, MN (US)

(73) Assignee: Kobara Medical Inc., Eden Prairie, MN (US)

( * ) Notice: Subject to any disclaimer, the term of this patent is extended or adjusted under 35 U.S.C. 154(b) by 11 days.

(21) Appl. No.: 16/036,844

(22) Filed: Jul. 16, 2018

(65) Prior Publication Data

US 2018/0326204 A1 Nov. 15, 2018

Related U.S. Application Data

(63) Continuation of application No. PCT/US2017/025662, filed on Apr. 1, 2017.
(Continued)

(51) Int. Cl.
*A61N 1/05* (2006.01)
*A61B 5/042* (2006.01)
(Continued)

(52) U.S. Cl.
CPC .......... *A61N 1/0587* (2013.01); *A61B 5/0422* (2013.01); *A61B 5/0464* (2013.01);
(Continued)

(58) Field of Classification Search
CPC ... A61B 5/0422; A61B 5/0464; A61B 5/6857; A61B 5/4836; A61B 2562/043;
(Continued)

(56) References Cited

U.S. PATENT DOCUMENTS

| 4,991,603 A | 2/1991 | Cohen et al. |
| 4,998,975 A | 3/1991 | Cohen et al. |

(Continued)

FOREIGN PATENT DOCUMENTS

| WO | WO2005039690 A1 | 5/2005 |
| WO | 2009062061 A1 | 5/2009 |
| WO | 2017027770 A1 | 2/2017 |

OTHER PUBLICATIONS

The International Search Report and the Written Opinion rendered by the International Searching Authority for PCT/US2017/025662, dated Jun. 21, 2018, 16 pages.

(Continued)

*Primary Examiner* — Aaron F Roane
(74) *Attorney, Agent, or Firm* — Skaar Ulbrich Macari, P.A.

(57) ABSTRACT

A cardiac lead system is provided. The lead is placed epicardially through the transverse pericardial sinus with integrated curvatures to prevent the lead from slipping out of the transverse pericardial sinus. Interaction with multiple chambers of the heart is facilitated in a single lead, without anchors that embed into the heart wall. Multiple electrodes can be grouped over each targeted heart area to ensure adequate electrical contact.

29 Claims, 16 Drawing Sheets

Related U.S. Application Data

(60) Provisional application No. 62/316,871, filed on Apr. 1, 2016, provisional application No. 62/409,857, filed on Oct. 18, 2016.

(51) Int. Cl.
*A61B 5/0464* (2006.01)
*A61B 5/00* (2006.01)
*A61N 1/39* (2006.01)

(52) U.S. Cl.
CPC .......... *A61B 5/6857* (2013.01); *A61B 5/4836* (2013.01); *A61B 2562/043* (2013.01); *A61N 1/0563* (2013.01); *A61N 1/3918* (2013.01); *A61N 1/3925* (2013.01); *A61N 1/39622* (2017.08)

(58) Field of Classification Search
CPC .............. A61N 1/0587; A61N 1/39622; A61N 1/0563; A61N 1/3918; A61N 1/3925
USPC .......................................................... 607/129
See application file for complete search history.

(56) References Cited

U.S. PATENT DOCUMENTS

| | | | |
|---|---|---|---|
| 5,324,321 A | 6/1994 | Pohndorf et al. | |
| 5,327,909 A | 7/1994 | Kiser et al. | |
| 5,397,342 A | 3/1995 | Heil, Jr. et al. | |
| 5,545,204 A | 8/1996 | Cammilli et al. | |
| 5,772,693 A | 6/1998 | Brownlee | |
| 5,957,966 A | 9/1999 | Schroeppel et al. | |
| 6,470,211 B1 | 10/2002 | Ideker et al. | |
| 6,556,873 B1 | 4/2003 | Smits | |
| 7,270,669 B1 | 9/2007 | Sra | |
| 7,448,999 B1 | 11/2008 | Karicherla et al. | |
| 7,783,352 B1* | 8/2010 | Ryu ..................... | A61N 1/3621 607/14 |
| 7,920,928 B1 | 4/2011 | Yang et al. | |
| 7,949,411 B1 | 5/2011 | Yang et al. | |
| 8,364,234 B2 | 1/2013 | Kordis et al. | |
| 8,406,902 B2 | 3/2013 | Morgan et al. | |
| 8,942,827 B2 | 1/2015 | Ollivier | |
| 8,983,601 B2 | 3/2015 | Fukamachi et al. | |
| 9,002,478 B1 | 4/2015 | Yang et al. | |
| 9,078,581 B2 | 7/2015 | Osypka | |
| 9,293,818 B2 | 3/2016 | Min | |
| 9,427,576 B2 | 8/2016 | Ollivier | |
| 9,572,977 B2 | 2/2017 | Ollivier | |
| 2007/0043412 A1 | 2/2007 | Janssens et al. | |
| 2007/0179540 A1 | 8/2007 | Stegemann et al. | |
| 2007/0239244 A1 | 10/2007 | Morgan et al. | |
| 2008/0051864 A1 | 2/2008 | Callas et al. | |
| 2008/0065185 A1 | 3/2008 | Worley | |
| 2008/0294229 A1 | 11/2008 | Friedman et al. | |
| 2009/0299447 A1 | 12/2009 | Jensen et al. | |
| 2010/0241185 A1 | 9/2010 | Mahapatra et al. | |
| 2011/0106070 A1* | 5/2011 | Fischer ................. | A61B 18/02 606/21 |
| 2012/0221072 A1 | 8/2012 | Fukamachi et al. | |
| 2012/0330092 A1 | 12/2012 | Shiose et al. | |
| 2013/0012938 A1* | 1/2013 | Asirvatham ............ | A61N 1/20 606/41 |
| 2014/0058470 A1 | 2/2014 | Shelton | |
| 2014/0330327 A1 | 11/2014 | Thompson-Nauman et al. | |
| 2015/0134042 A1 | 5/2015 | Ollivier | |
| 2016/0030757 A1 | 2/2016 | Jacobson | |
| 2016/0051322 A1 | 2/2016 | Asirvatham et al. | |
| 2016/0121102 A1 | 5/2016 | Tockman et al. | |
| 2016/0136433 A1 | 5/2016 | Stahmann et al. | |
| 2016/0228713 A1 | 8/2016 | Bar-Cohen et al. | |
| 2017/0043155 A1 | 2/2017 | Marshall et al. | |
| 2017/0056648 A1 | 3/2017 | Syed et al. | |
| 2019/0117960 A1 | 4/2019 | Marshall et al. | |

OTHER PUBLICATIONS

Rohan N. Kumthekar, MD et al., Minimally invasive percutaneous epicardial placement of a prototype miniature pacemaker with a leadlet under direct visualization: a feasibility study in an infant porcine model, Heart Rhythm Society, 1547-5271, pp. 1-7, Apr. 12, 2019.

The extended European Search Report rendered by the European Patent Office for European Patent Application No. 17776896.7(regional phase of PCT application No. PCT/US20171025662), dated Oct. 30, 2019, 6 pages.

\* cited by examiner

SHAPED EPICARDIAL LEAD AND PLACEMENT SYSTEM AND METHOD

PRIORITY

This Application is a continuation application of PCT Patent Application No. PCT/US2017/025662, filed Apr. 1, 2017, which claims priority to and the benefit of U.S. Provisional Patent Application No. 62/316,871, filed Apr. 1, 2016, and U.S. Provisional Patent Application No. 62/409,857, filed Oct. 18, 2016; with each of the above-referenced applications and disclosures incorporated fully herein by reference.

FIELD OF THE INVENTION

The present invention relates generally to devices that continuously monitor a patient's cardiac rhythm and deliver electrical pulses to the heart if and as needed. More specifically, the present invention relates to epicardial leads that monitor electrical signals from the epicardial surface of the heart, that delivers electrical energy, or both.

BACKGROUND OF THE INVENTION

In the field of cardiac medicine, minimally invasive therapies for treating conditions at the heart's external surface, or epicardium, have been developed or contemplated using epicardial leads. However, currently marketed epicardial lead designs have major drawbacks.

The first drawback is that current epicardial leads require a more invasive surgical approach to gain access to the epicardium and to be able to fixate the leads into the heart wall. The most minimally invasive conventional procedure is a video assisted thoracoscopic procedure (VATS), which is still considered a surgical method. It involves providing two access holes into the chest with the patient under general anesthesia. The first access hole is for the thoracoscope, which is placed in position to visualize the heart by reaching through the patient's left side and collapsing the left lung. The second access hole is used for the epicardial lead delivery. This approach is surgical in nature, requires anesthesia and puts the patient on single lung ventilation, all of which result in longer hospitalization, higher costs, higher morbidity and present the risk of other complications. Because of the nature of the access approach, this technique also limits where the leads can be placed, resulting in non-optimal placement of epicardial leads—e.g., intended left ventricular pacing.

The second drawback to conventional techniques is the securing of the lead in its intended position, which is with sutures in combination with active fixation type anchors. This involves trauma to the heart wall and, even though the fixation is into the tissue, there are still signal capture issues. As a result, it is not uncommon that two epicardial leads are implanted to help lower the signal capture thresholds. Lower signal capture thresholds are important to reduce power levels that affect battery life. Also, any time tissue such as the myocardium is penetrated, an inflammation response occurs, which is why conventional leads today have embedded steroids to manage the tissue response. The addition of a drug to the implant complicates the development, regulatory approval, and manufacturing of these leads. The anchoring methods described are similar to those used for endocardial leads and are one of two methods, where the anchors are integral to the electrodes to improve the signal measurement and delivery as much as possible. The first is a passive fixation method often described as a "fish hook" anchor that uses bristle-like tines on the lead to anchor the lead to the intra-cavitary pectinate muscles. The second is an active fixation method often described as a "screw-in" or "corkscrew" anchor. Endovascular leads, on the other hand, that go into small vessels such as the coronaries can have inherent winding curvatures or spirals intended to distend the vessel, to increase the frictional interaction and thereby help improve the electrical contact with the electrodes and provide positioning fixation of the lead. The St. Jude Quartet™ Quadripolar lead is an example of a commercially marketed lead with these spiral shape features. The epicardial space does not have such tissue constraints all around the leads.

The third drawback of current epicardial leads is that the number of contacts or electrodes is limited and local to attachment to the heart wall. Currently, there is only one site for pacing or sensing and it is generally done at the left ventricle epicardial location with permanent leads. However, often the therapy needs to be directed to multiple points, such as on atria and ventricles. Also, with only a few electrodes limited to a local region, there is no ability to implement advanced signal interpretation algorithms to improve therapy delivery—e.g., reducing inappropriate shocks for devices and leads with defibrillation. Since currently marketed devices have the primary electrodes integral or very near the fixation anchor, multiple epicardial leads must be used to get more than one electrode in contact with the heart wall. Bipolar epicardial leads are the only marketed examples today that exist (such as from St. Jude Medical or Greatbatch), which have a second electrode. However, it is in immediate proximity to the electrode anchored to the heart wall.

Examples of current epicardial lead products that have these aforementioned drawbacks include the CRT-Myopre lead by Greatbatch Medical and the Epicardial MP lead by Oscor Inc. Their use has been very limited due to these and other drawbacks.

With the introduction of new minimally invasive subcutaneous implantable cardioverter defibrillators (S-ICD's) there is an increased need for developing minimally invasive epicardial leads that do not require a surgical implantation approach. Subcutaneous ICD implantation has been the most recent advancement in ICD technology and has several advantages: it spares the higher risk intravascular approach, it provides access to the heart when intravascular access is not available or possible such as contra-indications like infection, and it leaves veins available for access for other indications. Although subcutaneous ICD devices have good sensing capabilities suitable for the intended ICD therapies such as defibrillation, there are many patients who are not ideal candidates as the ECG (electrocardiogram) criteria does not hold well for their candidacy. Also, current devices lack pacing capability. This limits their usefulness because the target patients for these devices have advanced heart conduction system disease even in the absence of heart block that requires pacing for heart rhythm management.

Endovascular based pacing leads have limitations as well. The current traditionally-placed coronary sinus leads used for endovascular left ventricle (LV) pacing for cardiac resynchronization are limited not just by the presence of coronary sinus branches and their caliber, but also by the challenges associated with implantation. Accordingly, outcomes are limited due to the limitations for pacing. Even leadless endovascular pacing devices have severe complication risks, including heart wall perforation and dislodgement.

Finally, there are no left atrial pacing or sensing systems which could enable right atrium to left atrium synchronization.

U.S. Pat. No. 8,942,827 contemplates a multi-electrode design based on a distributor housing from which branches of electrodes extend. However, it still requires fixation to the heart wall and therefore has similar drawbacks to current leads. U.S. Patent Publication No. 2007/0043412 also describes multiple electrodes along branches that extend outward. Here too, fixation of the multiple lead branches and electrodes poses significant challenges.

These epicardial lead examples and their associated implantation techniques are not well developed because they are surgical in nature and, consequently, more invasive. This, in turn, makes them less likely to be adopted and considered. In the past, electrode patches were used for pacing at multiple sites, which involves even more invasive sternotomy or thoracotomy procedures. Patches have largely been abandoned with the advent of intravenous leads that are far less invasive in comparison.

All the identified challenges have limited the implementation of epicardial leads. As such, what is needed is not just a multi-electrode lead but a single-lead multi-electrode construct that can be delivered with minimally invasive methods into the pericardial space using a catheter lumen, and that can be positioned across multiple areas of the epicardial surface of the heart without penetrating the heart wall or tissue.

SUMMARY OF THE INVENTION

The present invention solves many of the drawbacks mentioned herein by providing a single-lead multi-electrode and zones to allow placement over the different chambers of the heart (e.g., right and left atria, and right and left ventricles). This provides a more comprehensive therapy that includes not just pacing, which is typically done by energy exchange with the ventricle heart wall, but also synchronization of the chambers to further improve heart beating function.

The invention described herein is a single epicardial lead with multiple zones of electrodes, which is placed through the transverse pericardial sinus using an integrated shape-positioning feature to prevent the lead from dislodgement from the transverse pericardial sinus. Use of the transverse pericardial sinus as a structure for positioning, sensing, and pacing electrodes is advantageous. The lead shape-positioning feature interfaces with the exterior margins of the anatomy that creates the transverse pericardial sinus to prevent the lead from slipping out of the transverse pericardial sinus. The lead has multiple electrodes along its length that constitute multiple electrode groups or zones intended to be placed in the pericardial space and through the transverse pericardial sinus, to stay in close proximity with the visceral pericardium/myocardium, and against the epicardium. The electrode zones are spaced along the length of the lead to position each one over specific chambers of the heart.

The pericardial space (sometimes also called the epicardial space) is a potential space with a very small amount of fluid that provides just enough lubricity for the heart to move in the pericardium during beating. The pericardium protects the heart from the surrounding anatomy. The pericardial space between the pericardium and the heart epicardium is quite small (typically <1 mm), and the pericardium that surrounds the heart does not stretch very much because it is a fibrous tissue (unless it is a slow process of cardiac enlargement due to disease).

The present epicardial lead invention can be any shape and size, but can be round in cross-sectional shape and greater in diameter than the pericardial space in certain embodiments. As such, the pericardium presses the lead against the epicardial surface of the heart. The novel lead positioning-shape feature of this invention is specifically adapted for interfacing against either or both exterior margins of the transverse pericardial sinus through which the lead is intended to be placed. The transverse pericardial sinus is a rather narrow pathway in the pericardial space that connects one side of the heart near one atrium through the junction of several veins and arteries—e.g., between the pulmonary arteries and aorta, to the other side of the heart near the other atrium.

The present epicardial lead invention has a parent condition that represents its natural unstressed, predefined, state and shape. In certain embodiments, the lead has portions of winding back-and-forth or undulating curvatures. The overall gross parent shape can be straight in one plane, or curved in one or more planes, and can vary in curvature along the length of the lead to conform to the surface of the heart. The lead stiffness is low enough that it can be straightened for delivery through a catheter sheath, using what is known as an "over the wire" technique, and low enough that the strength and stiffness of the pericardium can make the lead largely conform to the shape or profile of the heart.

The delivery method for the present invention can rely on methods where, for example, an angioplasty guidewire, that is typically around 0.014" in diameter, is inserted down a central lumen in the lead and used as a rail to advance the lead. As one example of a delivery method, a steerable sheath is placed in the pericardial space using conventional minimally invasive pericardial access techniques. A steerable electrophysiology catheter is advanced through the steerable sheath. The transverse pericardial sinus is then accessed, utilizing the maneuvering functions of both the catheter and the sheath while using fluoroscopic imaging—primarily left anterior oblique (LAO) and right anterior oblique (RAO) views.

Once the catheter is in the transverse sinus behind or posterior the great vessels (aorta and pulmonary trunks), the catheter is further advanced close to the right atrioventricular junction on the lateral side. Then, the sheath is advanced over the catheter, while keeping the catheter in position. Once the sheath is in place, the catheter is removed and the angioplasty guidewire is inserted and advanced generously further past the sheath. Then, the lead is advanced over the guidewire inside the sheath using fluoroscopy for guidance through the transverse sinus and close to right atrial (RA) and right ventricle (RV) junctions. With the guidewire and lead in place, the sheath is gradually retracted, making sure the lead stays in the desired position. Once the sheath is completely removed out of the body, the guidewire can be slowly retracted and removed out of the lead, while keeping the lead in the desired position. The lead remains in position over the heart by itself because the inherent positioning-shape features of the lead prevent it from slipping out of the narrower transverse pericardial sinus.

Electrodes along the length of the lead are pressed against the epicardial surfaces by the pericardium, because the lead diameter or size is generally greater than the pericardial space. Also, the curvature of the lead itself provides self-passive fixation with the abutting pericardial sac. If additional contact force is desired, the portions of the lead where the electrodes are located can incorporate curvatures in the parent shape of the lead. The size, shape and spacing of the curvatures can vary and each one can be rounded to minimize irritation to the contacting tissue. In addition, the size of the positioning-shape features just distal or proximal to the transverse pericardial sinus can be greater than the sinus opening to keep the lead in position over the heart—e.g., at least two times the opening. With this type of positioning, the lead will lay on top of different areas of the heart so that electrodes placed along the length can be organized into zones that enable multiple sensing and stimulation combinations. The portion of the lead along which the electrodes are located can comprise a sequence and combination of winding back-and-forth curvatures, spiraling curvatures, straight sections, undulations, and the like. The winding curvatures themselves can include a curvature along the long axis of the lead, or its transverse or radial axis. These secondary curvatures make the lead inherently more conformable to the heart surface in its parent unstressed state and are compressed by the pericardium, which in turn presses the electrodes onto the epicardium.

Alternatively, there are other mechanical means by which lead positioning, relative to the transverse pericardial sinus, can be fixed. Rather than utilizing shape features of the lead itself, other means such as flanges, balloons, ribs, and like elements or features can be included to provide the necessary interference at the margins of the transverse pericardial sinus to minimize displacement of the lead. These may be fixed in position to the lead or have a means for adjusting their position along the length of the lead. For example, an internal shape memory or formable wire segment may be inserted along an internal lumen, thereby shifting the position of positioning-shape feature along the axis of the lead.

The lead exits near the access site where it is easily and safely sutured in place using a suture sleeve attached to subcutaneous tissue accessible by the clinician from outside the patient. This provides the second anchoring location of the lead. The remaining proximal end of the lead is channeled subcutaneously to the final site of the active implantable device, which is typically implanted either sub-pectoral infraclavicular or axillary as is common for new subcutaneous ICDs. Alternatively, the epicardial lead invention may have integrated electronics or components as a means for wireless activation by an ICD so that tunneling is not necessary. It can also be potentially tunneled to pectoral implants, which are currently performed for intravascular leads for pacing and sensing.

The lead can enter the pericardial space near the xiphoid and follows an inferior-posterior track to the left entrance of the transverse pericardial sinus, and then crosses through to the medial side. In this way, three or four potential sensing and stimulation zones are created—e.g., one over the right atrium (RA), one over the left atrium (LA), Bachmann bundle, and one over the left ventricle (LV). For each zone, one or more electrodes can be placed to ensure at least one electrode is in good contact with the epicardial surface, or used to pace to avoid phrenic nerve capture. The distal end of the lead that is past the transverse pericardial sinus is over the right atrium along which there are preferably at least one (1) electrode or zone. There can be at least one (1) electrode, but preferably four (4) in some embodiments, positioned over the left atrium as well, which is just proximal the transverse pericardial sinus. The section of the lead that extends from there to the entry point lies over the left ventricle, along which there can be at least one (1) electrode positioned—and four (4) in various embodiments. The proximal end of the lead then exits the pericardial space through the pericardium to then be routed subcutaneously to the active implantable device as previously detailed. The multiple electrode or zone pacing and sensing capability of the present invention makes this lead unique to assess various locations for best pacing and sensing, as well as to avoid phrenic nerve pacing as the lead crosses through the transverse sinus towards the subxiphoid region.

The course of the lead in the pericardial transverse sinus enables pacing especially Bachmann bundle, which is novel from the pericardial space and helps for atrial synchrony. A further benefit is that the present invention can avoid unwanted phrenic nerve capture, since the phrenic nerve mostly traverses antero-laterally and this epicardial invention lead takes a postero-later position which is not near the phrenic nerve. Another benefit is that the multiple electrodes provide opportunity for choosing different electrodes and for multi-point pacing of the left ventricle. Yet another major advantage is the lead provides left ventricular pacing, as opposed to right ventricular pacing, which has hemodynamic advantages and resynchronization capacities.

The leads of the present invention can be further enhanced with the addition of various features that improve performance, effectiveness, and safety. One enhancement is a lead construction that allows variation in the spacing of electrode zones to accommodate anatomical variations. For example, the distance between electrode zones for the left and right atria may be increased or decreased to better fit a patient's heart. Another embodiment of this invention can be constructed using multiplexing electronics and circuitry with individually addressable electrode positions. This enables the lead electrode configuration to be customizable to the patient receiving the therapy and reduces the required number of connection points at the proximal end so that there can be more electrodes throughout the length of the lead than proximal connection electrodes. Another enhancement is designing the lead such that the conductive surfaces of the electrodes face away from the parietal pericardium. This reduces the chances of unintended stimulation or capture of the phrenic nerves that run along the pericardial membrane.

Different cardiac therapies with this single epicardial lead invention can now be implemented with the arrangement of electrodes in the multiple zones detailed herein. First, the left atrium and right atrium can be synchronized, which is unique to this technology. Second, the left ventricle can be stimulated for pacing with sensing from the left atrium or right atrium electrodes. Third, the left ventricle and atria can be synchronized, as opposed to Right Atrium (RA) and Left Ventricle (LV)+ Right Ventricle (RV) lead synchronization in traditional cardiac resynchronization therapy devices. Fourth, by placing the stimulation zones of the lead along the transverse pericardial sinus, pacing interventions for neuromodulation purposes can be implemented by stimulating the ganglionated plexi in the transverse pericardial sinus area. Fifth, a stimulation zone of the lead can be replaced with a defibrillation or shocking coil to incorporate defibrillation capabilities into the lead, which is preferably placed over the ventricle. Sixth, by comparing the signals between different electrodes it is possible to better discern and differentiate arrhythmias, such as Inappropriate Sinus Tachycardia (IST), Atrial Tachycardia (AT), Atrioventricular Nodal Reentrant Tachycardia (ANRT), Atrial Fibrillation (AF), Atrioventricular Reentrant Tachycardia (ART), and Atrial Flutter (AFL).

Figure 1:
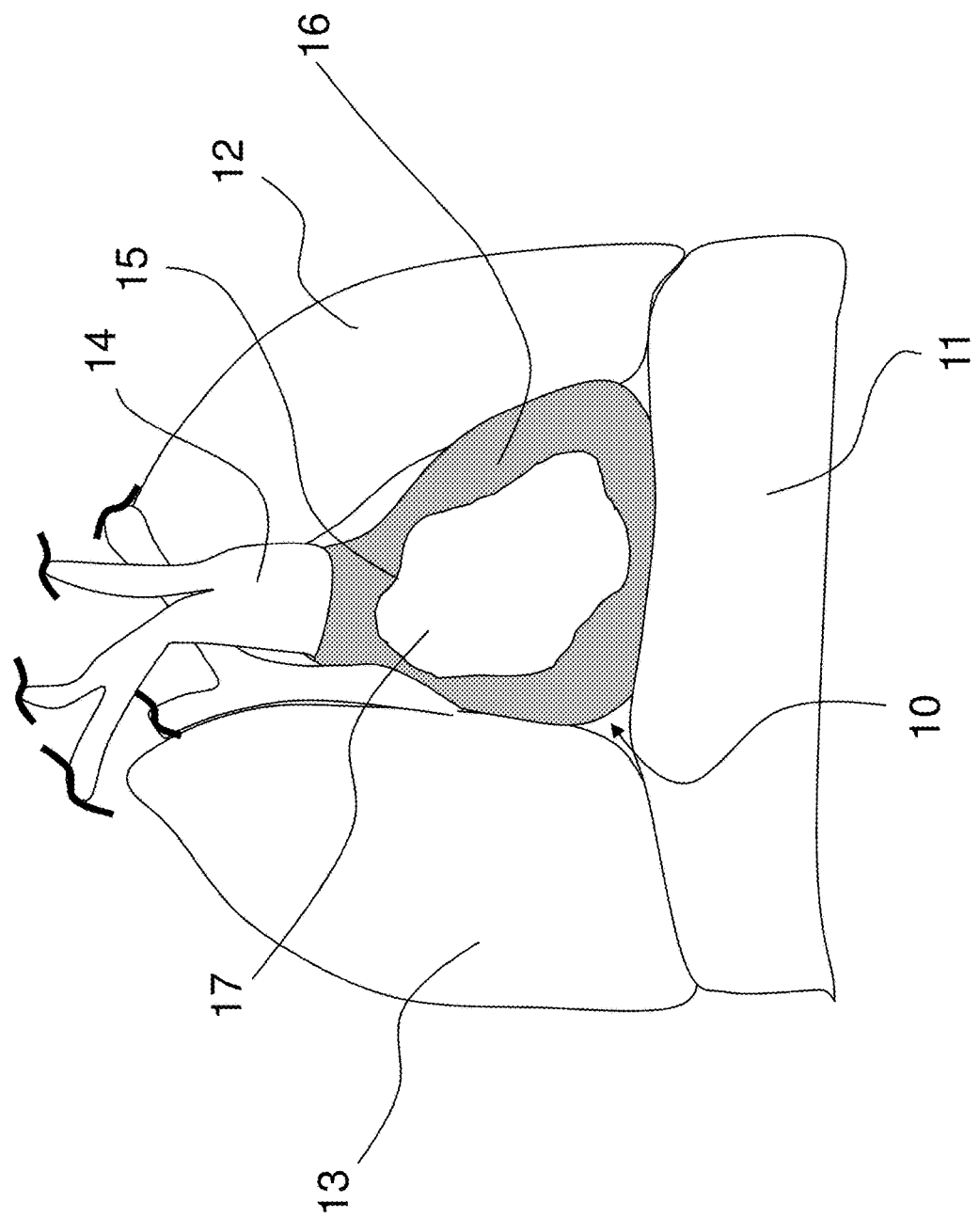
FIG. 1 is an anterior view of the thoracic cavity with a portion of the pericardium removed to show the epicardial surface of the heart.

While the invention is amenable to various modifications and alternative forms, specifics thereof have been shown by way of example in the drawings and will be described in detail. It should be understood, however, that the intention is not to limit the invention to the particular embodiments described. On the contrary, the invention is to cover all modifications, equivalents, and alternatives falling within the spirit and scope of the invention as defined by the appended claims.

DETAILED DESCRIPTION

Exemplary embodiments of the present invention are described in the following, with reference to the drawings. It should be understood that such embodiments are by way of example only and merely illustrative of the many possible embodiments which can represent applications of the principles of the present invention. Various changes and modifications obvious to one skilled in the art to which the present invention pertains are deemed to be within the spirit, scope, and contemplation of the present invention as further defined in the appended claims. The exemplary embodiments of the present invention described herein are not intended to be exhaustive or to limit the present invention to the precise forms disclosed in the following detailed description. Rather, the exemplary embodiments described herein are chosen and described so those skilled in the art can appreciate and understand the principles and practices of the present invention.

Referring to FIG. 1, an anterior view of the thoracic cavity, the pertinent anatomical structures such as the heart 10, diaphragm 11, left lung 12, right lung 13, and aorta 14 are shown. A portion 15 of the parietal pericardium 16 is cut away to show the underlying epicardium 17. The pericardial space is the space between the parietal pericardium 16 and the epicardium 17.

Figure 2:
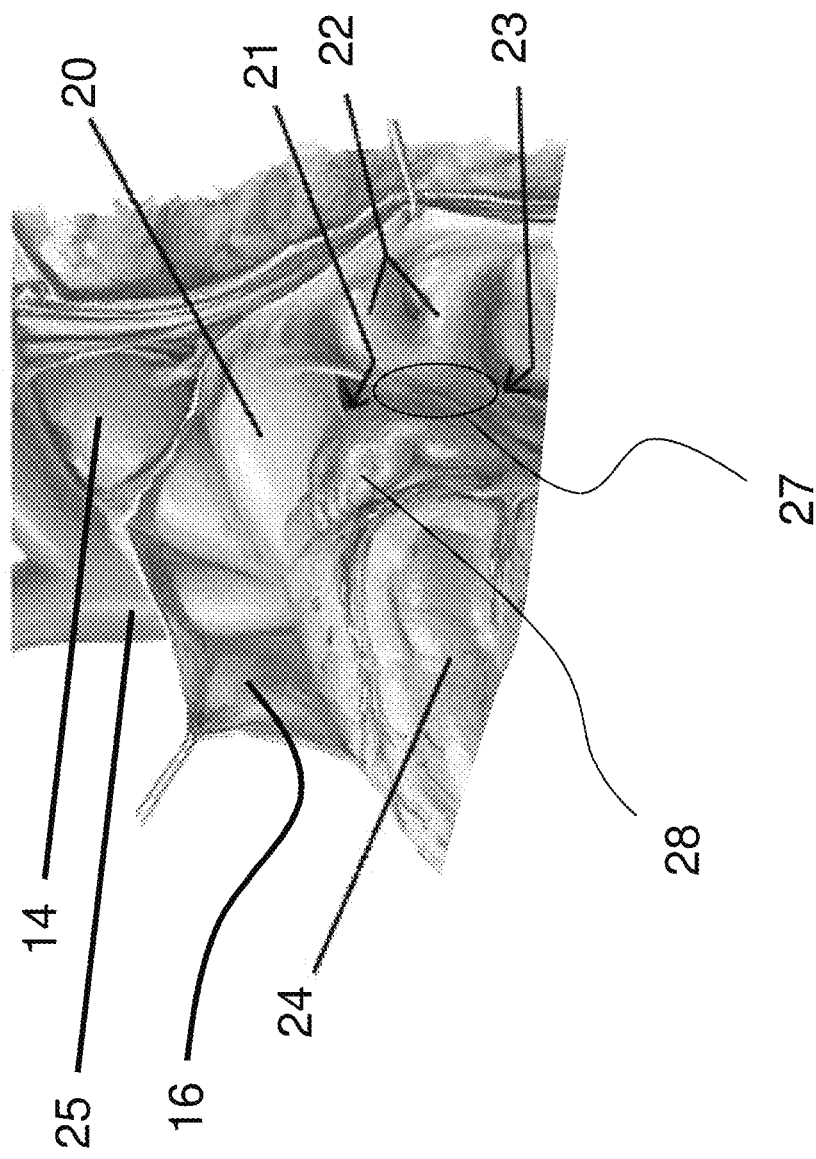
FIG. 2 shows the pericardium reflected back near the great vessels of the heart to show the proximal entrance of the transverse pericardial sinus.
Figure 3:
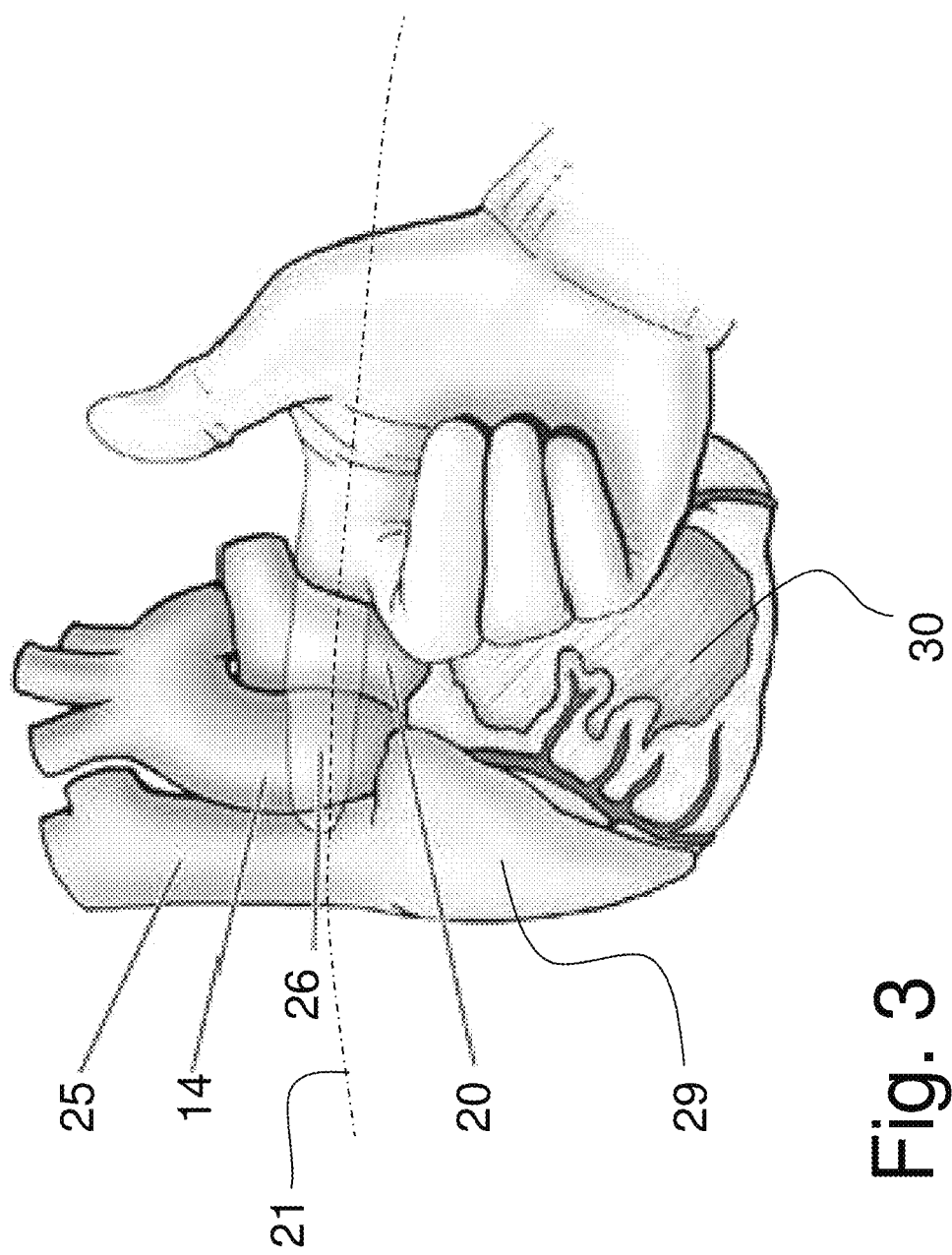
FIG. 3 illustrates a schematic of the heart with a finger through the transverse pericardial sinus as a way to show its position relative to anatomic landmarks.

Referring now to FIG. 2, the pericardium 16 is reflected back to allow visibility of the great vessels (aorta 14 and pulmonary trunk 20), the transverse pericardial sinus 21 (proximal entry point which is towards the left lateral side), the left pulmonary veins 22, the oblique pericardial sinus 23, the left ventricle 24, the left atrial appendage 28, and the superior vena cava 25 (which connects to the right atrium 29 that is visible in FIG. 3). The epicardial lead of the present invention has multiple zones of electrodes that are intended to be placed on epicardial surfaces associated with any combination of, or all of, the four key chambers of the heart: right atrium 29 (seen in FIG. 3), left atrium 27, left ventricle 24, and right ventricle 30 (seen in FIG. 3). With various embodiments, the preferred combination of chambers is the right atrium 29, the left atrium 27, and the left ventricle 24.

FIG. 3 shows a finger 26 placed through the transverse pericardial sinus 21 as a way to better visualize it, and its relationship to key anatomical landmarks such as the superior vena cava 25 at its distal end, the aorta 14, and the pulmonary trunk 20 at its proximal end. The transverse pericardial sinus 21 is posterior to the aorta 14 and pulmonary trunk 20, and is the key anatomical space into which this epicardial lead of the present invention is placed. The transverse pericardial sinus 21 space can be small, but illustrating a finger through the space shows that the surrounding tissue and vessels can be distended to about 1.5 cm to 2 cm (e.g., the width range of a typical finger) to make a snug fit with the finger. In this figure, the right ventricle 30 is seen.

Figure 4:
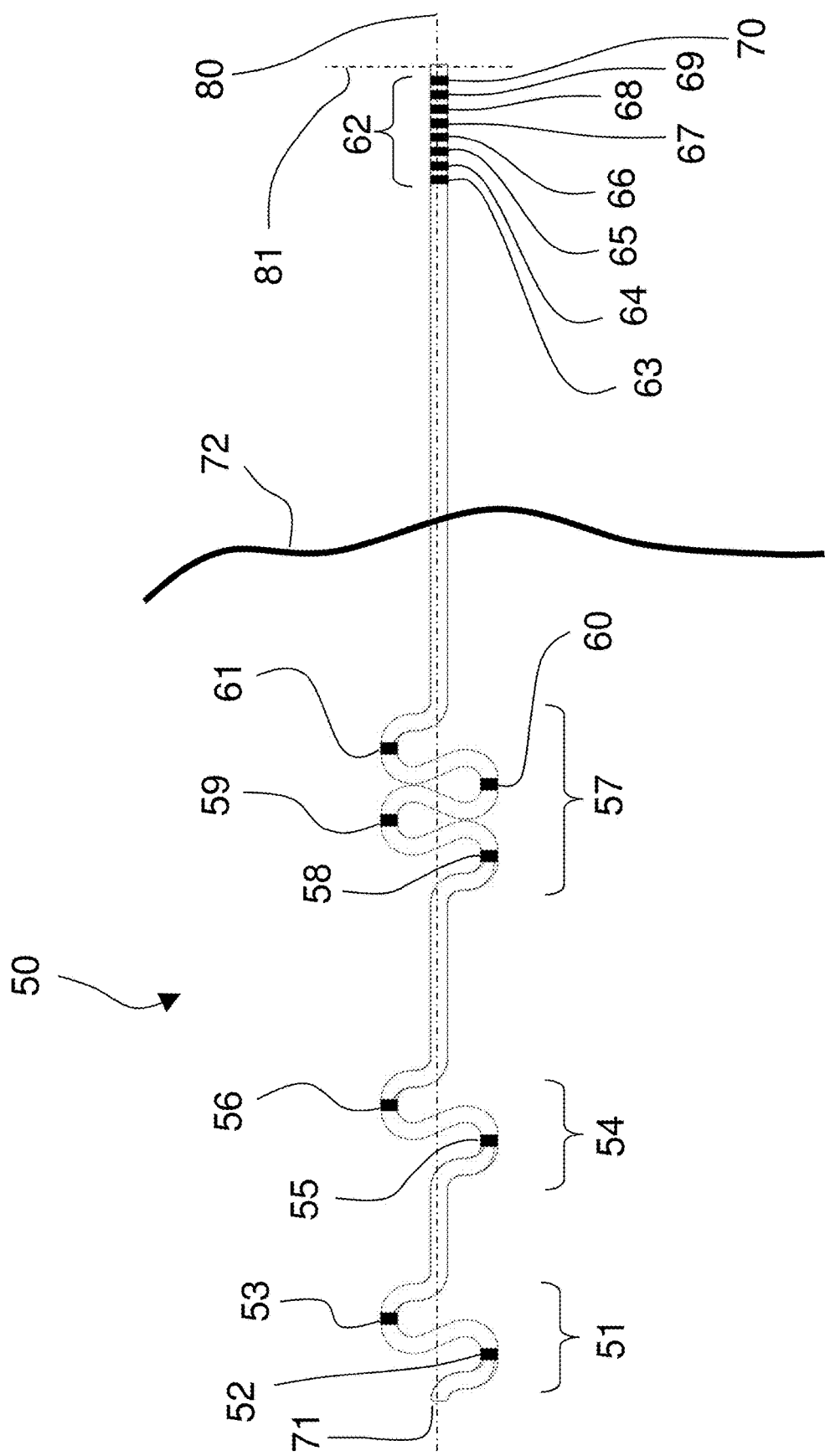
FIG. 4 is a top view of a straight (or straightened) embodiment of the present invention with winding back-and-forth or undulating curvatures, with electrodes provided along its length, and with the distal group of electrodes acting as a shape-positioning feature.

FIG. 4 shows an embodiment of the epicardial lead 50 having a long axis 80 and transverse axis 81 located at the proximal-most end of the lead 50. The lead 50 as shown is laid out straight along its long axis 80, but can have overall curvatures, and other shape characteristics as well. Starting at distal end 71, positioned just distal of the transverse pericardial sinus (not shown), the lead 50 has three groups of tissue-contacting electrodes: distal group 51, mid group 54, and proximal group 57. The first distal group 51 includes individual electrodes 52 and 53. The second mid group 54 includes individual electrodes 55 and 56. The third proximal group includes individual electrodes 58, 59, 60 and 61. Each of these electrodes operatively connects to a corresponding electrode (e.g., 63 through 70) of the connector-end group of electrodes or contacts 62, which plugs into or is otherwise operatively connected to an active implantable device connector. The lead 50 crosses into the pericardial space between the proximal electrode group 57 and the connector-end group 62, shown in this figure by pericardium margin 72. The lead 50 outside the pericardium can be sutured to fascia to fixate the proximal end of the lead 50. While various lead constructs, and electrode lead shapes, sizes, and groupings, are shown, other configurations and group numberings can be employed without deviating from the spirit and scope of the present invention.

The electrode groups 51, 54, and 57 of lead 50 have curvatures or arcuate orientations in the direction of the transverse axis 81 that wind back and forth with the individual electrodes of each zone located at the outer most portion of the curvature. The electrodes can be located anywhere along the lead 50, but in this particular embodiment they are shown along the winding curvatures. Multiple electrodes in each group 51, 54, and 57 are incorporated to improve the chance that at least one electrode has adequate contact with the epicardial surface.

If the lead 50 is positioned with the back-and-forth winding curvature of electrode group 51 in the transverse pericardial sinus 21 (see FIGS. 2 and 3), then there is friction and interference type engagement with the surrounding great vessels, depending on the diameter of the lead, the width of the windings, the stiffness of the lead, the size of the sinus, the stiffness of the tissue, etc. In this way, the other electrode group 54 is either in the transverse pericardial sinus as well, or proximal to it in the pericardial space. The third electrode group 57 would then be in the pericardial space. This type of placement relies on a friction or interference (or both) fit between the winding curvature of the leads and surrounding tissue and vessels to prevent the lead from slipping out of the transverse pericardial sinus.

The lead 50 cross-section shape can be of any form, but is shown round. A non-circular shape could be beneficial as the bending characteristics can be directional. The size of the cross-section can be greater than the pericardial space thickness, which is typically much less than 2 mm. In this way, the larger sized lead 50 will tend to be pushed inward by the pericardium, resulting in better contact between the electrodes and the epicardium.

Figure 5:
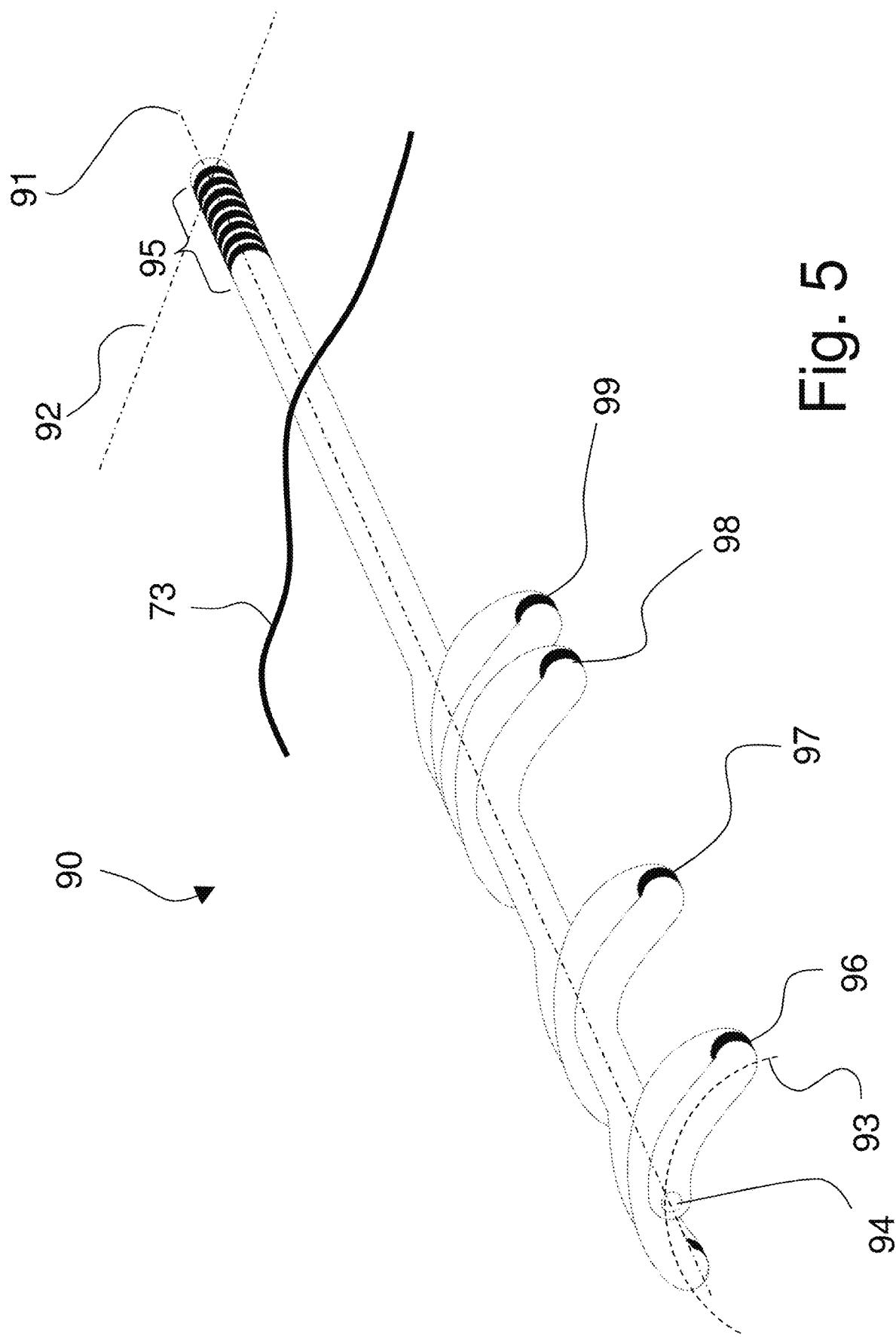
FIG. 5 is an isometric view of an embodiment of the present invention showing transverse curvatures added to the long-axis winding curvatures to increase contact force of the electrodes to the epicardial surface of the heart.

The force on the lead against the epicardium can be increased by creating an inherent curvature in the group of leads 51, 54, and 57 along the transverse axis 81. FIG. 5 shows an embodiment with lead 90 straightened out along longitudinal axis 91, which has the same electrode configurations as lead 50 of FIG. 4, but having an inherent curvature 93 along the transverse axis 92. In the view in this figure, the distal end 94 is shown along with a plurality of tissue-contacting electrodes 96, 97, 98, and 99. The same number of electrodes can be included on the opposing side, but are not readily visible in this view. Each one of these electrodes operatively connects to a contact in the connector-end group 95, like that presented in FIG. 4. Lead 90 also crosses into the pericardium at the margin 73 in a similar way. The lead 90 overall is intended to be compliant relative to surrounding tissue, and the tautness of the pericardium will inherently deform this transverse axis curvature 93, creating more force on the electrodes of lead 90 against the epicardium than a lead without transverse curvature 93 (e.g., flat). For electrodes such as 96 and 97 that may be in the pericardial sinus, this helps ensure they are pressing against epicardial tissue in the transverse sinus.

Both of the aforementioned embodiments in FIGS. 4 and 5 rely on friction or interference (or both) to hold them in place if the distal electrode group is in the transverse pericardial sinus. Over time, however, the lead may slip because of the natural downward force of the weight of the lead and the beating motion of the heart. In the worst case, the lead slips out of the transverse pericardial sinus such that the distal group of electrodes are no longer positioned over the right atrium and the mid group are no longer over the left atrium. The proximal end of the lead exits the pericardium and is sutured in place so the proximal group electrodes will remain over the left ventricle.

Still referring to FIGS. 4 and 5, the spacing between the electrode groups can be adjusted so that the distal electrode group resides outside the transverse pericardial sinus, but still over the right atrium. If the curvature is wide enough in the transverse directions, the distal group curvature can limit or prevent the lead from slipping out of the transverse pericardial sinus.

Figure 6:
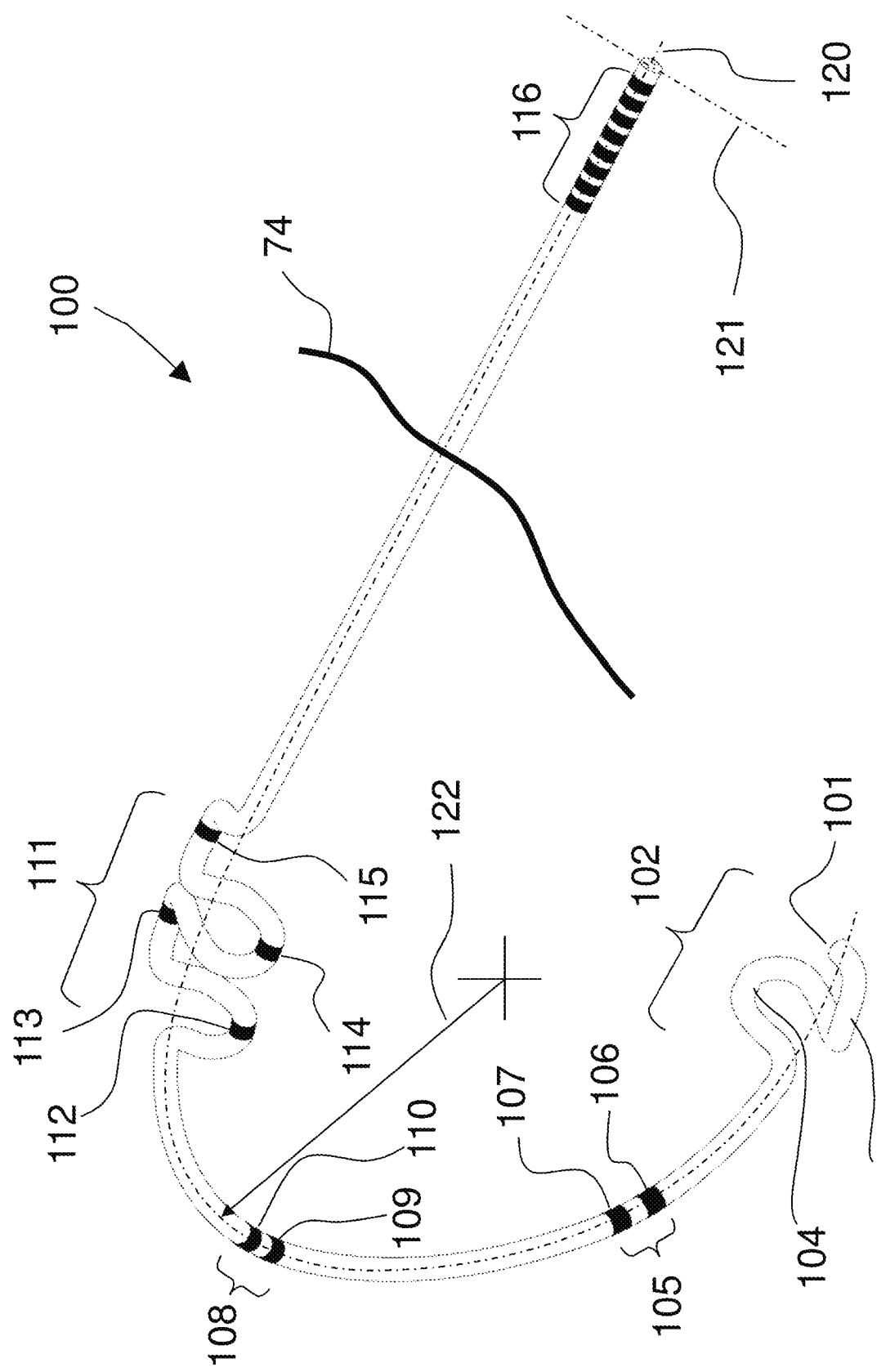
FIG. 6 is an isometric view of an embodiment of the present invention without electrodes along a shape-positioning feature, and having an overall rounded parent shape to better conform to the heart shape.

FIG. 6 shows an embodiment of lead 100 with alternate placement of the electrodes and back-and-forth windings. Lead 100 has longitudinal axis 120 and transverse axis 121. Lead 100 includes distal end 101 having positioning lead shape section 102 that is constructed with two preformed curvatures 103 and 104 extending outward along the transverse axis 121 directions. Positioning lead shape section 102 in this embodiment can exclude electrodes. Proximal to this section 102 is the distal electrode group 105 having electrodes 106 and 107, followed by mid electrode group 108 having electrodes 109 and 110. Both of the electrode groups 105 and 108 are along sections of the lead 100, along the curving longitudinal axis 120. Proximal electrode group 111 includes electrodes 112, 113, 114, and 115 that are placed along winding curvatures that extend outward in the transverse axis 121 directions. All of the electrodes of groups 105, 108, and 111 can operatively connect to electrodes that are part of connector-end contact group 116. Here too, between the proximal group 111 and the connector-end contact group 116, the lead 100 transitions into the pericardial space at the pericardial margin 74. Lead 100 parent shape has an inherent curvature 122 that is shaped to match or to be similar to the shape or profile of the heart so that the tendency of the lead 100 to lift off the curved epicardial heart surface is reduced or eliminated. With each of the embodiments detailed herein, this parent or default initial shape can be the result of using various shape memory metals or like materials for all, or select portions of, the lead device.

Figure 7:
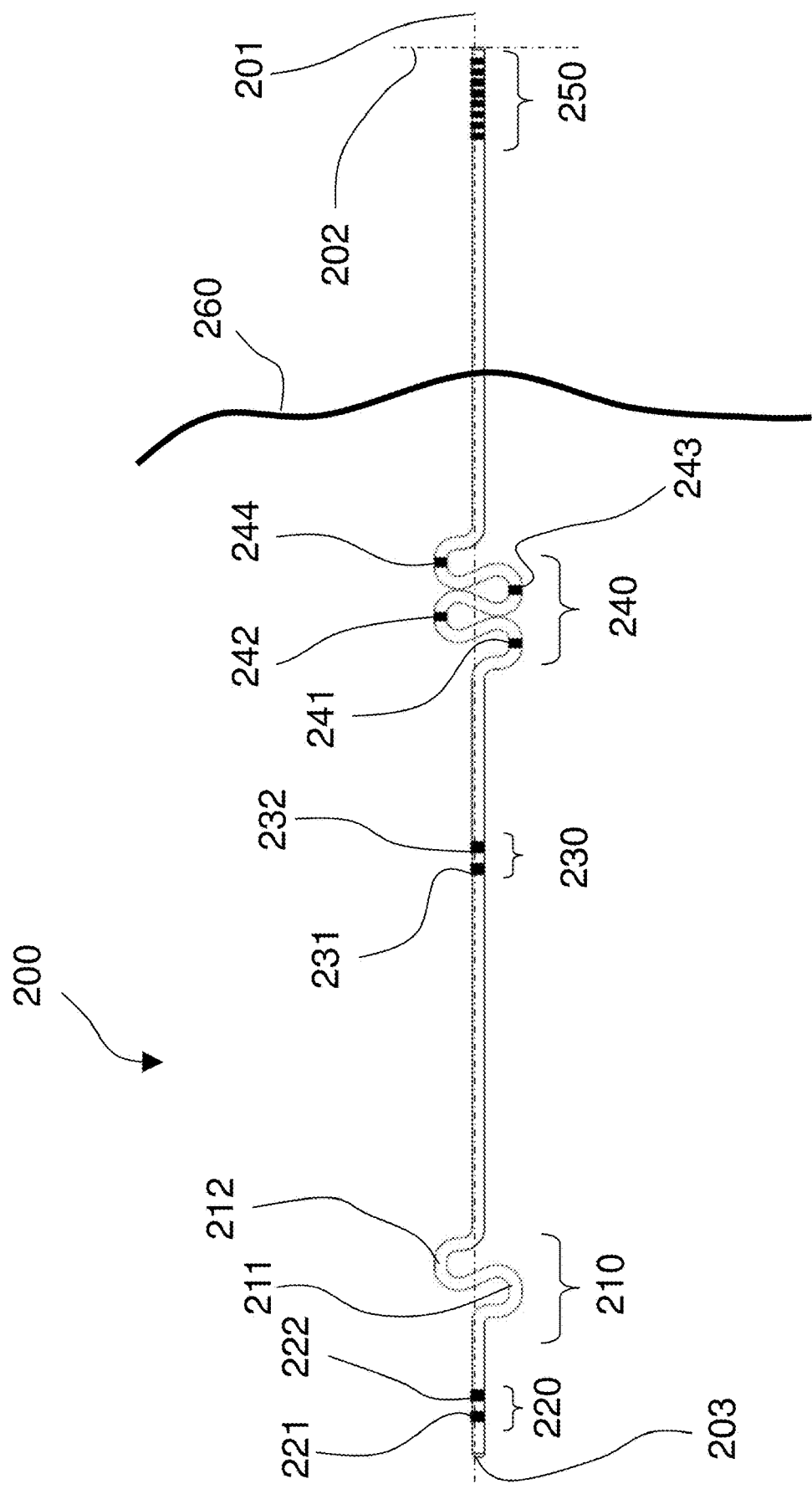
FIG. 7 is a top view of a straightened embodiment of the present invention with varying electrode placements.
Figure 8:
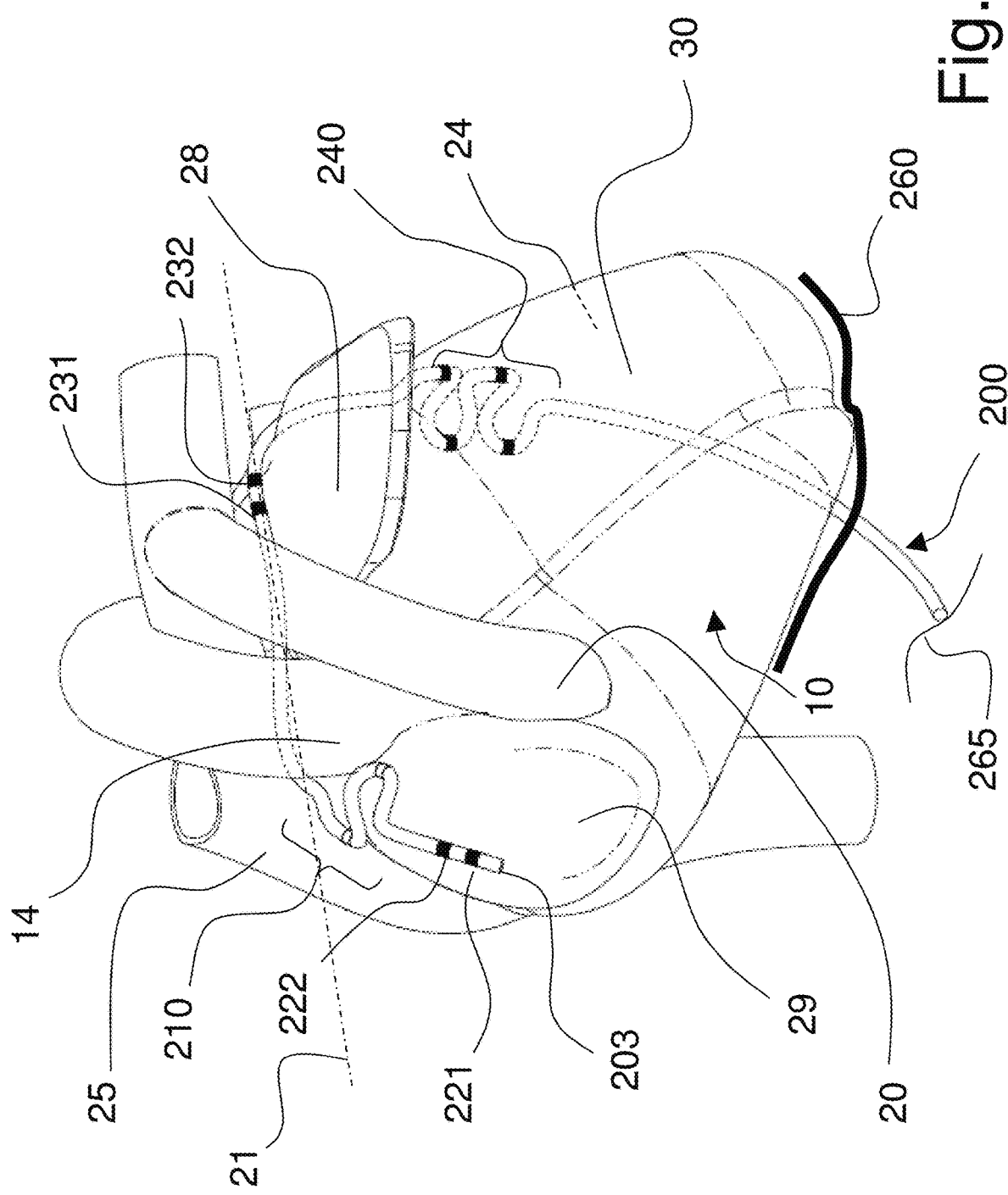
FIG. 8 is an isometric view of the embodiment of FIG. 7 placed onto a heart.

Referring to FIGS. 7 and 8, lead 200 is yet another embodiment having varying placement of the electrodes and back-and-forth windings. FIG. 7 shows a top view of lead 200 straightened, and FIG. 8 shows lead 200 implanted and how it would be positioned around a heart. Specifically, lead 200 includes longitudinal axis 201 and transverse axis 202. The lead 200 embodiment includes distal end 203 having positioning lead shape section 210 that is formed with two preformed curvatures 211 and 212, extending outward along the transverse axis 202 directions. Positioning lead shape section 210 in this embodiment is shown without electrodes but could be designed with electrodes as well. Distal to section 210 is the distal electrode group 220 having electrodes 221 and 222, followed by mid electrode group 230 having electrodes 231 and 232. Both of the electrode groups 220 and 230 are provided along sections of the lead 200 that are straight along the curving longitudinal axis 201, where the curvature is seen in FIG. 8. Proximal electrode group 240 includes electrodes 241, 242, 243, and 244 that are placed along winding curvatures that extend outward in the transverse axis 202 directions. All of the electrodes of groups 220, 230, and 240 can operatively connect to electrodes that are part of connector-end contact group 250 (shown in FIG. 7). Here too, between the proximal group 240 and the connector-end contact group 250, is where the lead 200 transitions into the pericardial space at the pericardial margin, a portion of which is shown as 260. Lead 200 parent shape can have an inherent curvature that is shaped to match the shape or profile of the heart so that the tendency of the lead 200 to lift off the curved epicardial heart surface is reduced or eliminated.

The lead 200 is preferably delivered into the pericardial space with a subxiphoid approach. FIG. 8 shows lead 200 placed on heart 10 (from FIGS. 1-3). The lead 200 is compliant and for delivery it approaches the right ventricle 30, where it enters into the pericardial space. Delivering it into the pericardial space requires sliding it into a sheath (e.g., the St. Jude Medical Agilis steerable sheath) that straightens it out. The distal end of the sheath is placed at the location where the distal end 203 of the lead 200 is to be located, which is just past the distal margin of the transverse pericardial sinus. The sheath is then retracted and as the lead 200 exits it inherently reforms or reshapes to take on its parent shape, but is constrained or meets resistance in part by the surrounding tissue with which it interfaces. The distal positioning lead shape section 210 ends up at the distal margin of the anatomical structures (e.g., superior vena cava 25 and aorta 14) that define the transverse pericardial sinus 21, thereby preventing the lead 200 from then sliding towards the proximal end of the transverse pericardial sinus 21.

The pulmonary trunk 20 that also defines transverse pericardial sinus 21 is shown in FIG. 8 as well. When the sheath is fully retracted, the distal electrode group 220 and mid electrode group 230 are positioned over the right atrium 29 and left atrium 28 epicardial surfaces, respectively. The proximal electrode group 240 is positioned over the left ventricle 24, and since this portion is merely covered by the pericardium, a transverse curvature can be included with this section (similar to that shown in the embodiment of FIG. 5) and would assist in pressing the electrodes against the epicardium of the left ventricle 24. In FIG. 8, the proximal end of the lead 200 is not shown beyond where it may be sutured to fascia 265, but could extend further. The proximal end having connector-end contact group 250 can be tunneled then to an implantable device. Alternatively, electronics could be incorporated into this portion of the lead so that tunneling is not required and the lead 200 communicates and works wirelessly with the implantable device.

Figure 9:
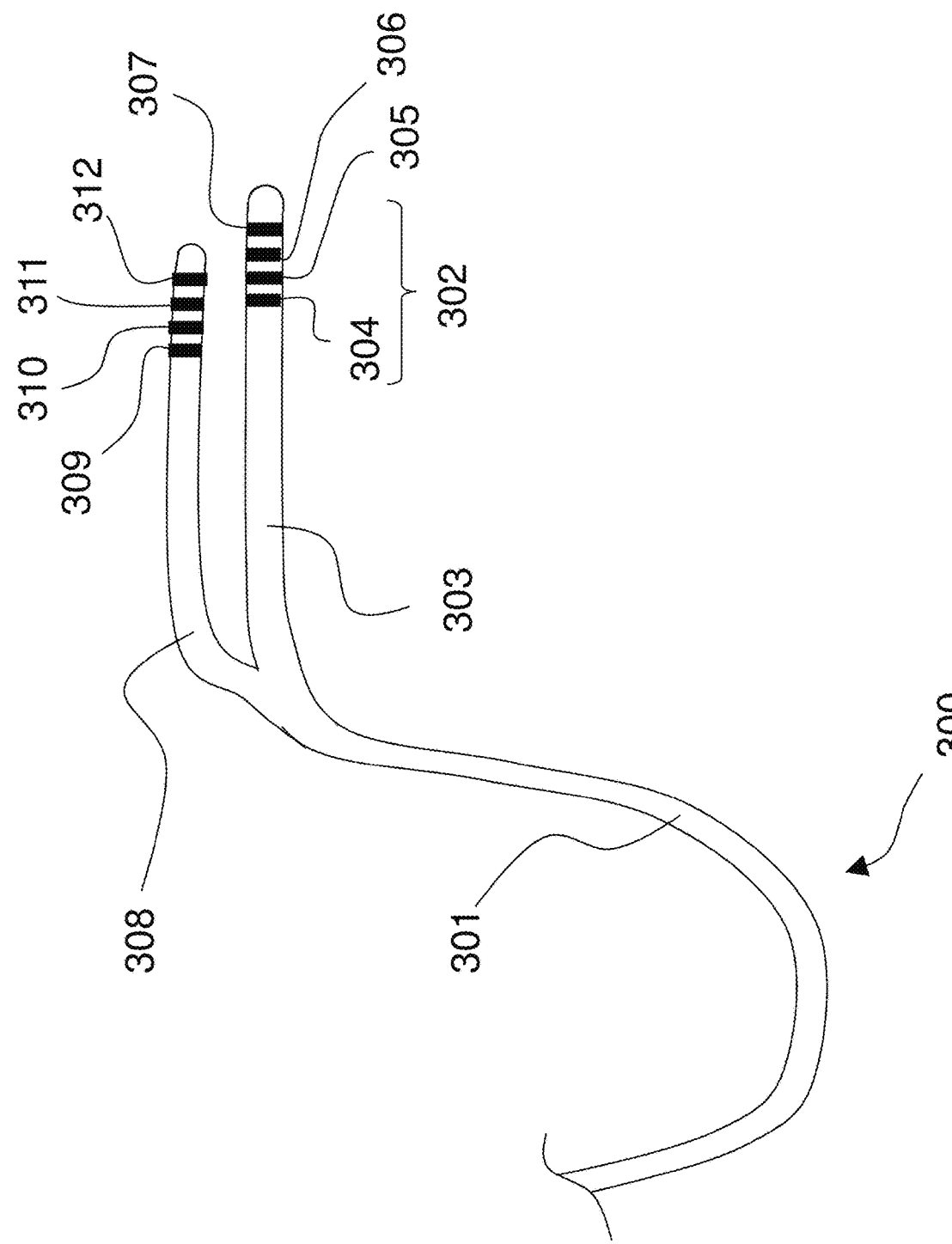
FIG. 9 is a top view of the proximal portion of the present invention as an embodiment with the lead splitting into two proximal connection ends.
Figure 10:
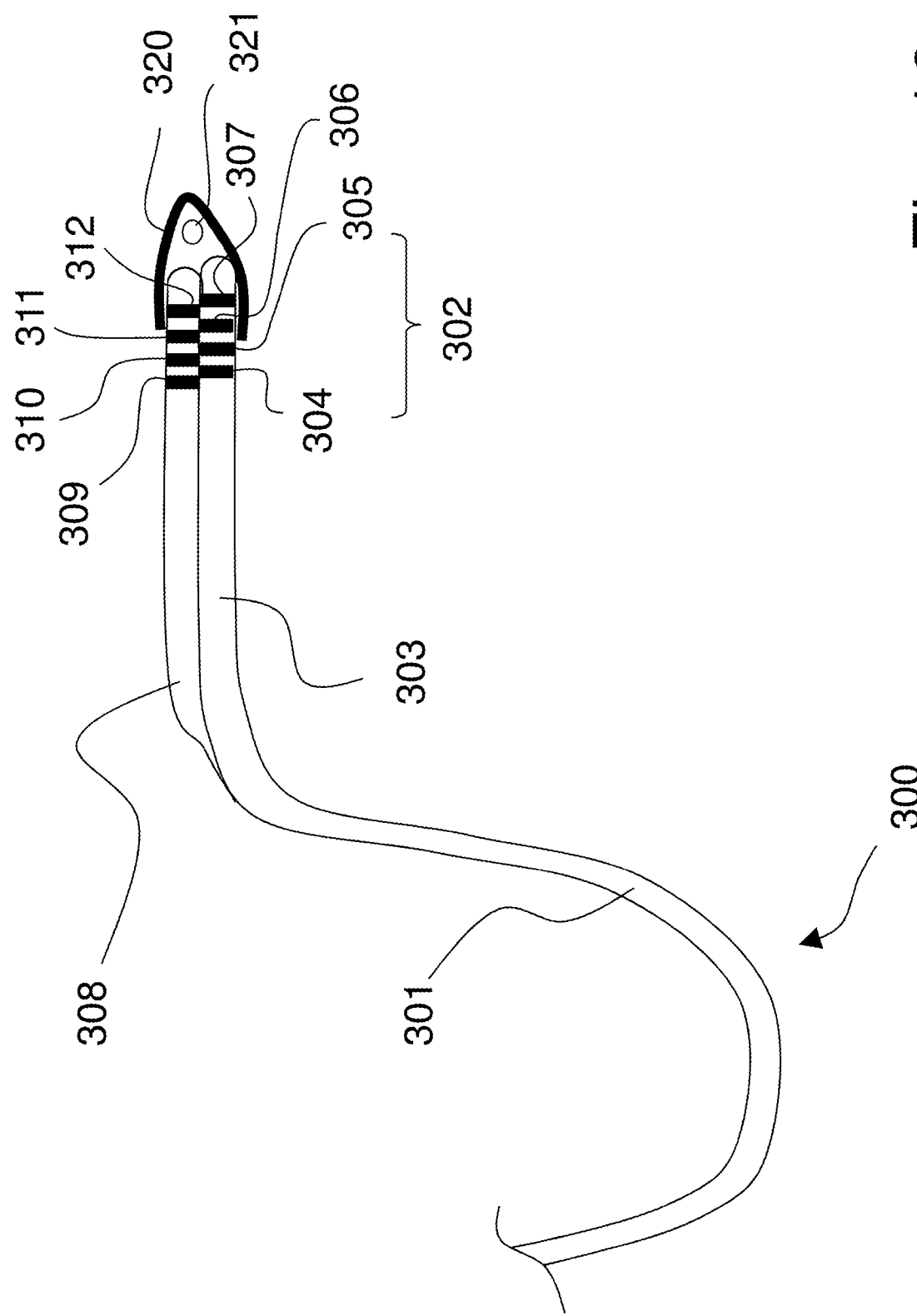
FIG. 10 is a top view of the embodiment of FIG. 9, with a cap provided over both proximal connection ends.

In various embodiments, where the lead must operatively connect directly to an implantable device rather wireless communicating with it, it may be necessary to split the proximal connector end 250 of lead 200 into two or more tails that operatively connect into an implantable device or devices. Such an embodiment is shown in FIGS. 9 and 10 as lead 300. The lead 300 can include a main body 301 that splits into two proximal connector end tails 303 and 308 that comprise proximal connector end 302. Assuming with certain embodiments that there are a total of 8 electrodes on lead 300, and half can go on one tail and half on the other, then tail 303 includes contacts 304, 305, 306, and 307, and tail 308 includes electrodes 309, 310, 311, and 312. Tunneling the connector ends 303 and 308 to the implantable area can be challenging. As a result, a removable cap 320 can be slipped over the two tails 303 and 308 such that they stay together and can be tunneled to an implantable area more easily (FIG. 10). A hold 321 can be included with cap 320 to allow a suture or like element to pass through or to be tied to cap 320—making it easier to pull through tissue.

It will be clear to those skilled in the art that the overall placement of the single lead across the left ventricle, then the left atrium through the transverse pericardial sinus and over the right atrium is unique and novel. The embodiments described hereinabove have localized shapes that were shown as winding back and forth curvatures. These curvatures can take on any form, including spiral, twisting, straight, arcuate, and the like. Any number of curvatures can be included with at least one curvature at the distal end to prevent the lead from slipping back through the transverse pericardial sinus.

Figure 11:
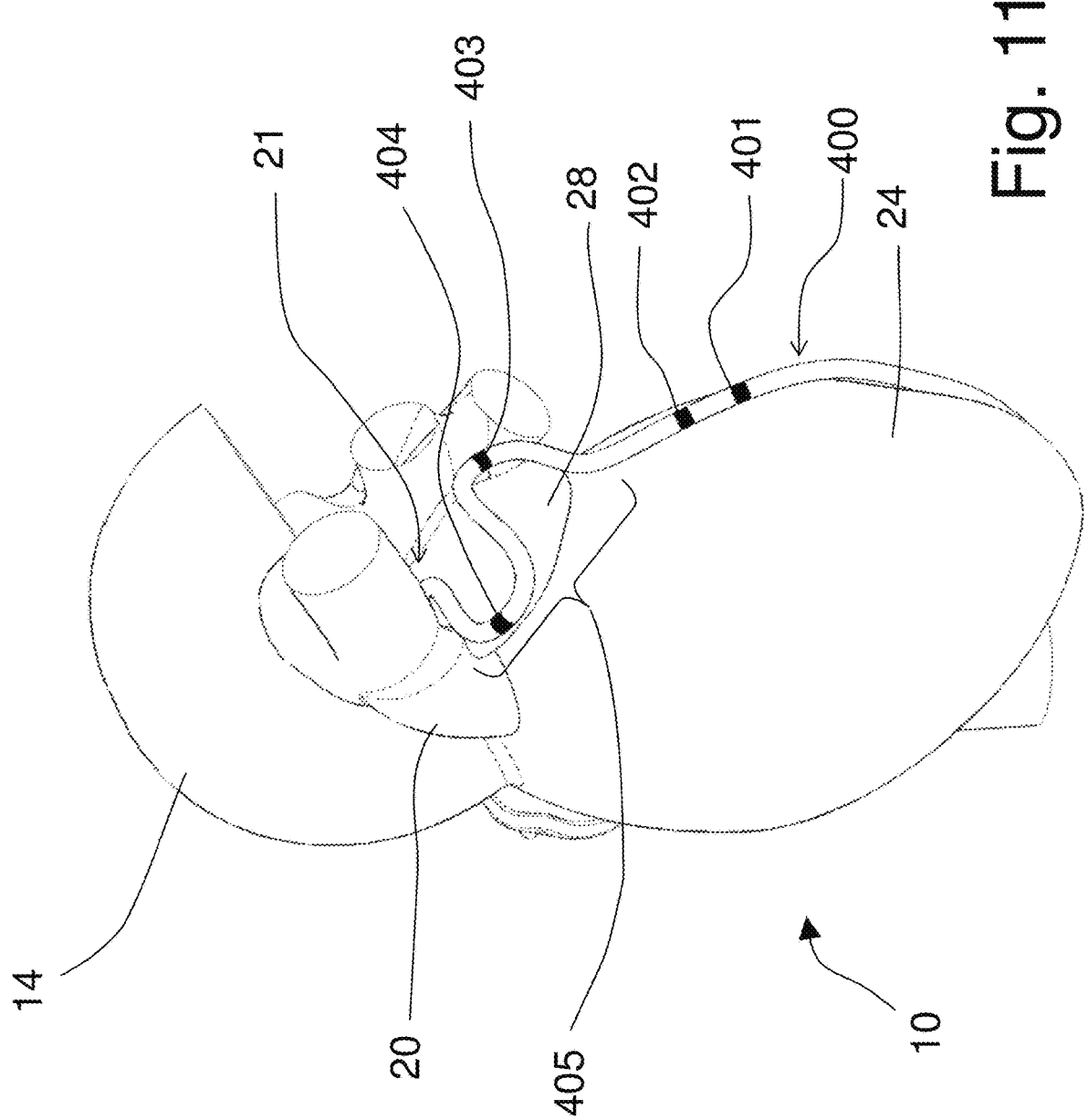
FIG. 11 is a left lateral view of the heart showing an element for a shape-positioning feature, in accordance with an embodiment of the present invention.

FIG. 11 shows an embodiment having an anchoring curvature located at the proximal end of the transverse pericardial sinus 21. A left lateral anterior view of the heart 10 is shown with left ventricle 24, left atrial appendage 28, left pulmonary trunk 20, and aorta 14 all visible. A portion of lead 400 that is positioned through the transverse pericardial sinus 21 is shown with electrodes 401 and 402 positioned over the left ventricle 24. Electrodes 403 and 404 are positioned over the left atrial appendage 28 and incorporated into curvature 405, which is adjacent the proximal entry of the transverse pericardial sinus 21. The curvature 405 prevents the lead 400 from moving further to the distal end (which is on the right side of the heart) of the transverse pericardial sinus 21.

Figure 12:
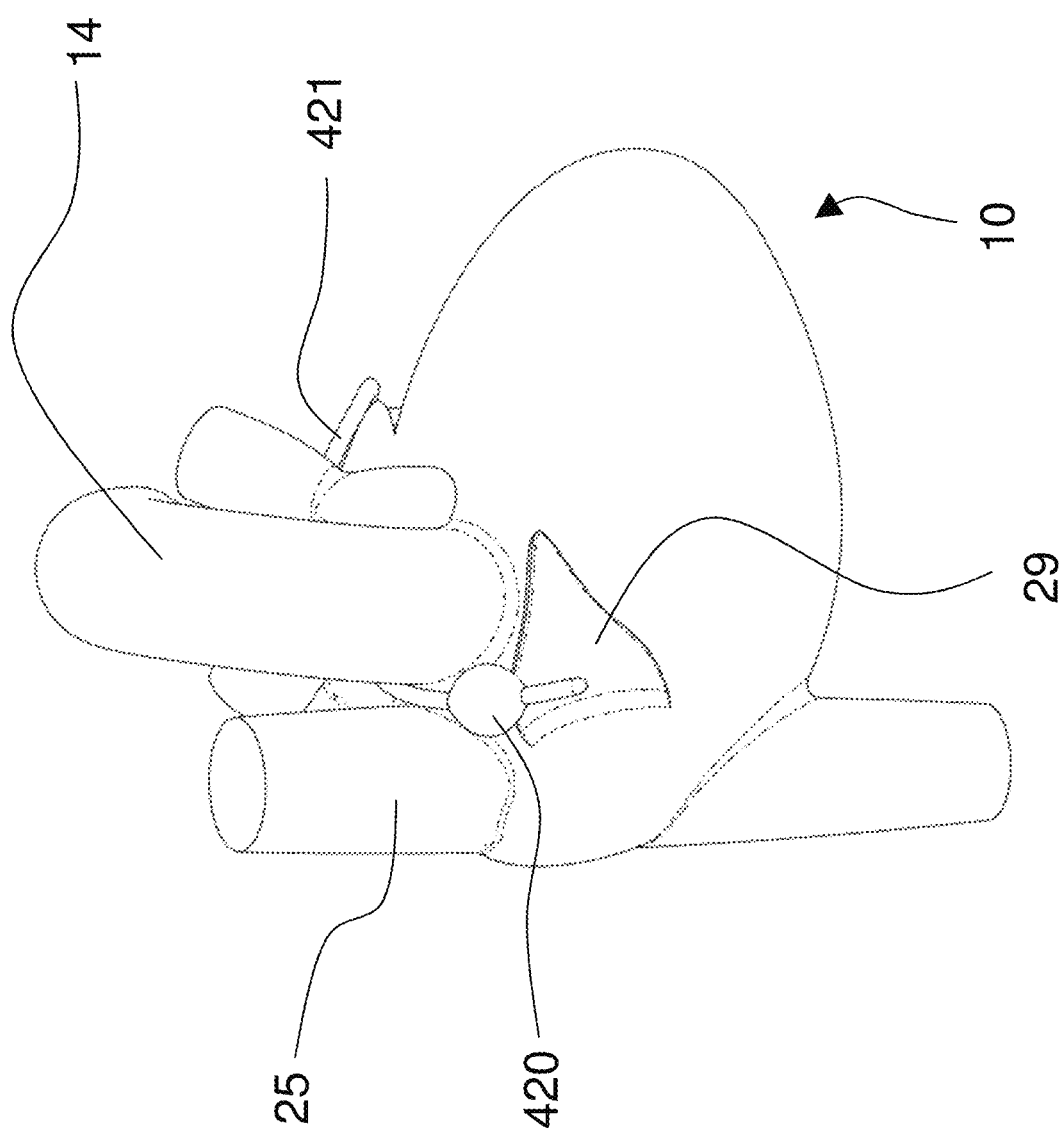
FIG. 12 is a right lateral view of the heart showing an element for a positioning feature that uses an expanding wall or balloon to prevent displacement of the lead, in accordance with an embodiment of the present invention.

FIG. 12 shows a right view of heart 10 with aorta 14, superior vena cava 25, and right atrial appendage 29 identified. In this figure, an embodiment of the atraumatic anchor is shown as an expanded element 420 such as a balloon, stent-like structure, and the like—instead of a curvature of the lead 421.

Figure 13:
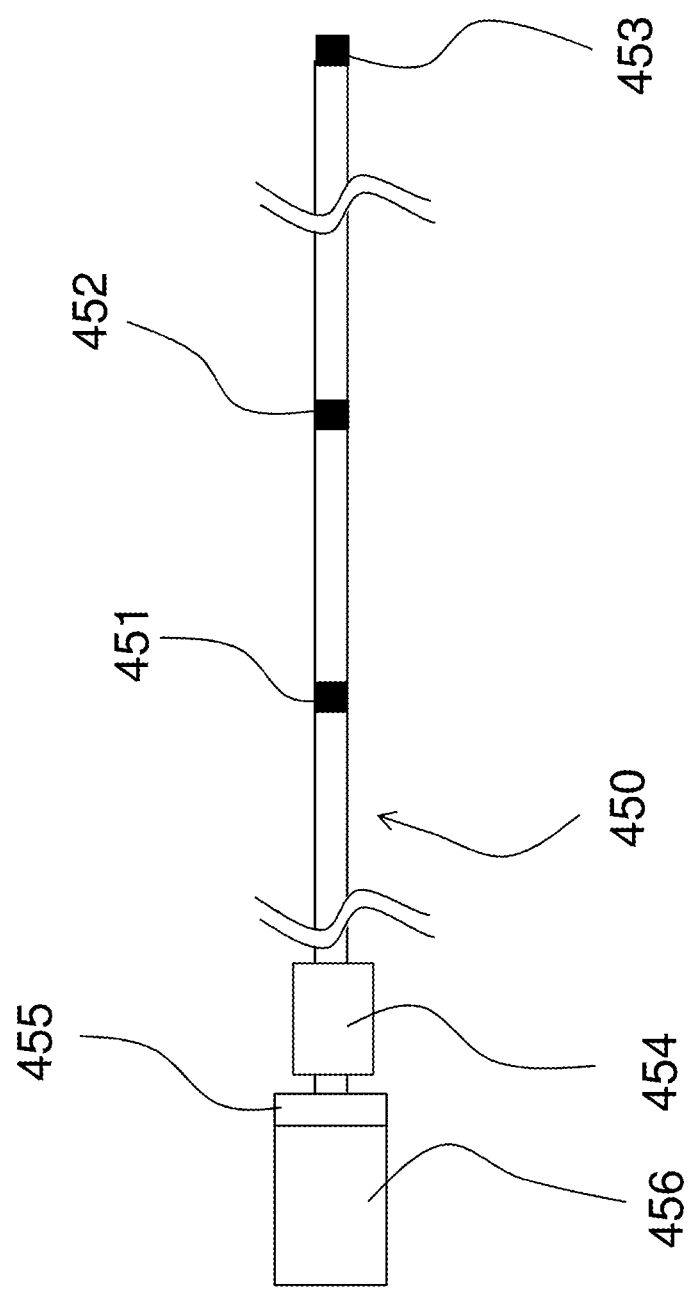
FIG. 13 shows a lead configured for multiplex electrode connections, in accordance with an embodiment of the present invention.

One advantage of the present invention is the ability to incorporate a plurality of electrodes along the length of the lead distributed across multiple chambers of the heart. Since a heart varies from person to person, it can be advantageous to incorporate many electrodes and then only use those specific electrodes that have better contact with the heart or are in a preferred location. When each electrode is operatively connected directly to a connector-end electrode (e.g., 62 in FIG. 4 as an example), then the number of connector-end group of electrodes increases as the number of electrodes increases. This can cause the implant connector to increases in size as well, which can be undesirable—especially if only a subset number of electrodes are actually used. An alternative embodiment of the present invention is shown in FIG. 13, illustrating the use of integrated circuits (ICs) to reduce the number of connector-end electrodes. Component 456 is an active implantable, such as an Implantable Cardiac Defibrillator (ICD) having connector 455. Lead 450 is shown with its proximal end mated or otherwise connected with the connector 455. One or more ICs, such as multiplexers shown as 454, are included with the lead 450 and allow for fewer connector-end electrodes than electrodes that contact the heart: 451, 452, through 453 (the nth electrode).

Figure 14:
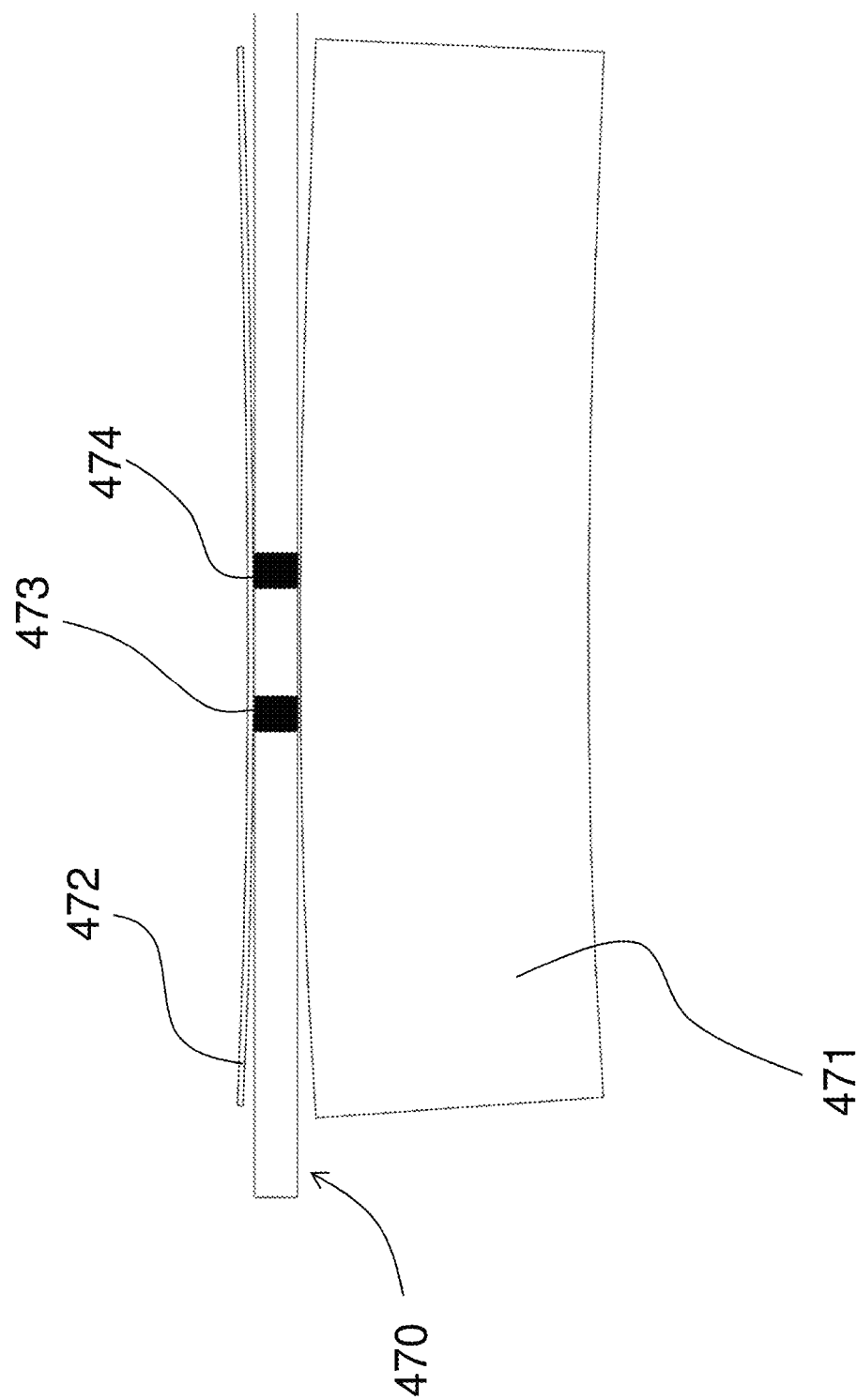
FIG. 14 is a detailed view of a segment of a lead, with section views of the heart wall and parietal perineal membrane, in accordance with an embodiment of the present invention.
Figure 15:
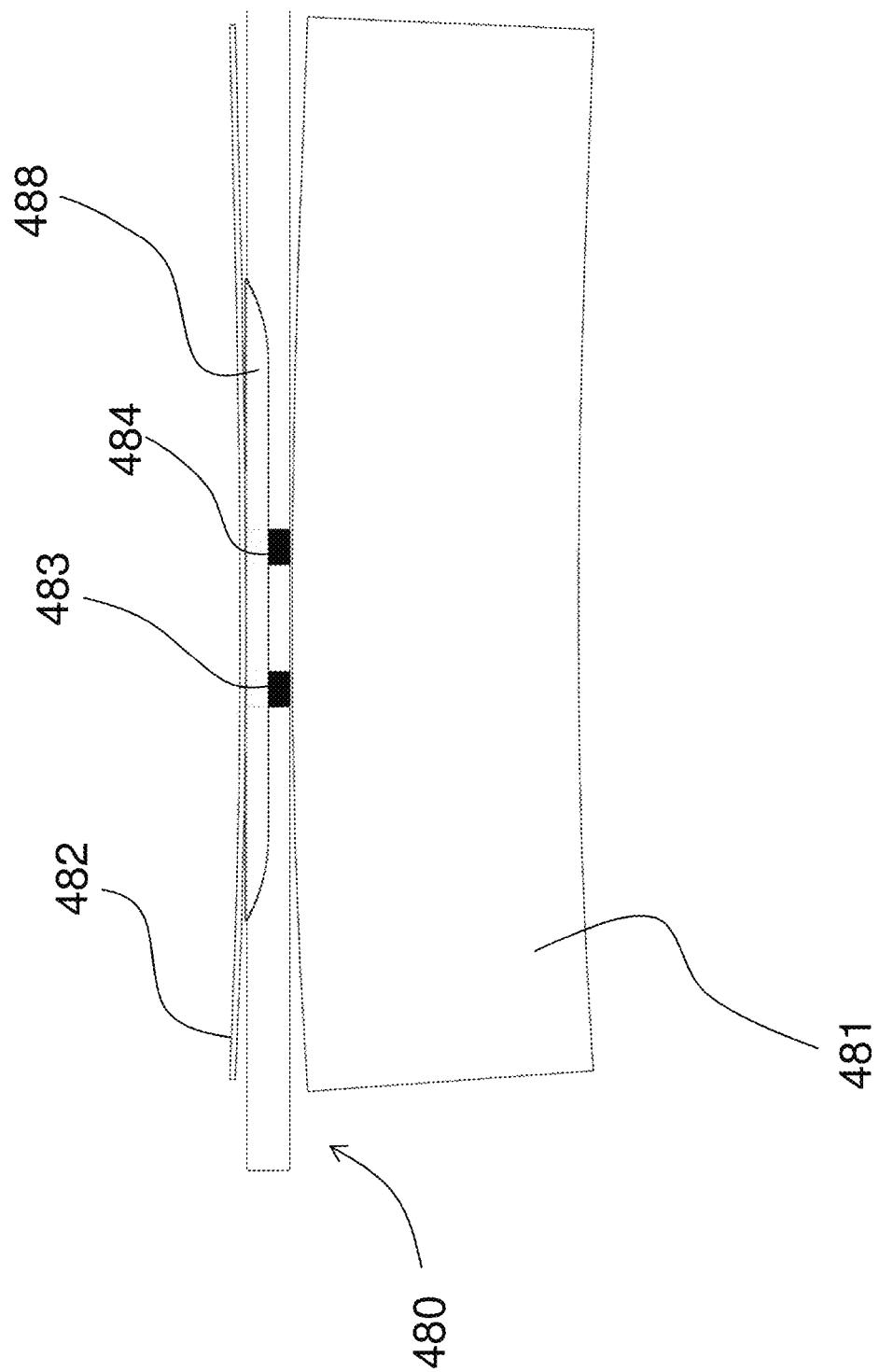
FIG. 15 is the detailed view depicted in FIG. 14, with the addition of an insulator that masks the side of the electrode facing the parietal perineal membrane, in accordance with an embodiment of the present invention.

FIG. 14 shows lead 470 configured similar to all of the aforementioned embodiments of the present invention, where electrodes 473 and 474 are a conductive material such as a metal circular ring and are fully circumferentially exposed to make contact with the heart wall 471 and the pericardium 472. There is a portion of the pericardium through which the phrenic nerve passes, which is part of the autonomous nervous system that controls breathing. If an electrode is positioned underneath or in close proximity to the phrenic nerve then it is desired to not activate the electrode, or to cover the outside surface of the electrode with electrically non-conductive material. FIG. 15 illustrates this embodiment where lead 480 has electrodes 483 and 484 that press against the heart wall 481. Those electrodes are covered with electrically non-conductive element 488 to prevent any electrical energy from passing into the pericardium 482.

Further, any number of electrodes or zones can be placed and have an effect on the overall diameter of the lead. Additionally, any number of electrodes or zones can be grouped and the groups can be spaced strategically so that they fall onto or contact any key location or chamber of the heart—e.g., right atrium, left atrium and left ventricle. Electrodes or zones can be combined with other features integrated into the lead—e.g., a defibrillation coil, a wireless communications and power module, etc. The lead construct here can utilize conventional manufacturing methods for cardiovascular leads so it can be mass produced at an effective and desirable cost.

Figure 16:
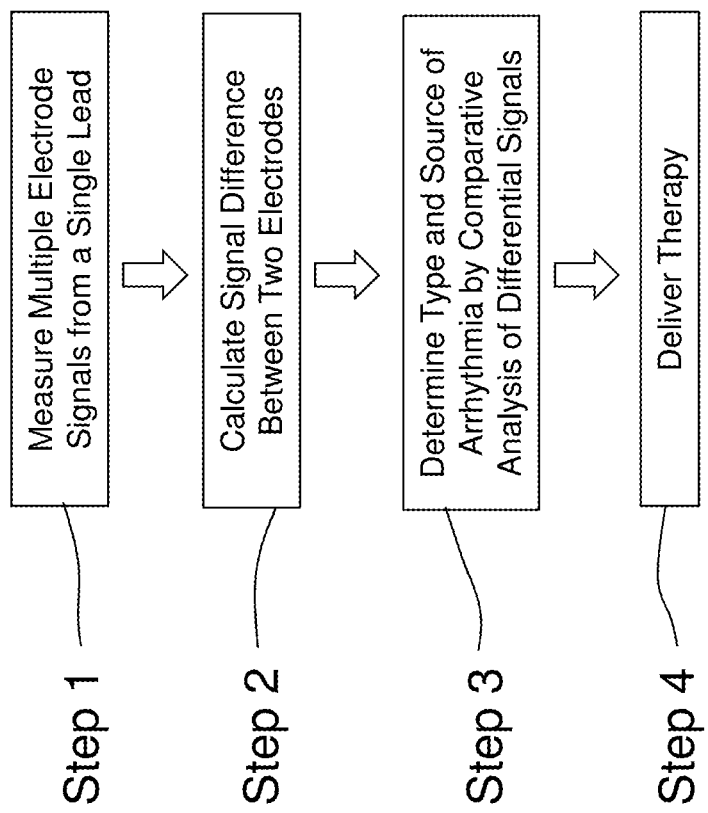
FIG. 16 is a flow diagram depicting a process for improved therapy delivery using multiple electrodes across multiple heart chambers, in accordance with an embodiment of the present invention.

As previously described, the present invention allows multi-site placement of electrodes across multiple heart chambers. The electrical signals measured from these electrodes can then be processed for improved therapy delivery. An exemplary methodology is shown in FIG. 16 as four steps. In Step 1, Measure Multiple Electrode Signals from a Single Lead, the device such as an ICD collects the signal data from each electrode as a function of time. In Step 2, Calculate Signal Difference Between Two Electrodes, the device can use the signal measurements and perform computations such as the signal amplitude difference between any two electrodes. The device can do this for all the electrode pair permutations. In Step 3, Determine Type and Source of Arrhythmia by Comparative Analysis of Differential Signals, the device can evaluate the measurements from Step 1 and the calculations from Step 2 to process and determine the type and source of the arrhythmia.

For example, if electrodes across the left ventricle show an arrhythmic signal originating from the Atrioventricular Node into the ventricle, then a Ventricular Tachycardia (VT) may be suspected. If electrodes over the right atrium together with electrodes over the left ventricle show a normal rhythm signal moving from the Sinus Node (SA Node) through the ventricle, then no arrhythmia is suspected, and therapy can be withheld. If the signal appears abnormal then a Supraventricular Arrhythmia is suspected, and specific therapy can be delivered. Since there are options to receive sensing signals from RA, LA and LV, it is extremely helpful in designing an algorithm to identify and differentiate the origin of arrhythmia so that, for example, defibrillator therapy can be tailored to appropriate rhythms based on various vectors and creating signature templates from the vectors created through different poles (electrodes) of the leads. As there is enough literature to indicate inappropriate shocks are deleterious and appropriate shocks are life-saving, the present invention will provide opportunity to optimize and enhance therapy options for patients. Having a better map of the heart conduction signals from an implanted lead can then be used for any future cardiac ablation procedures.

The delivery method for the present invention can rely on methods where, for example, an angioplasty guidewire, that is typically around 0.014" in diameter, is inserted down a central lumen in the lead and used as a rail to advance the lead. As one example of a delivery method, a steerable sheath is placed in the pericardial space using conventional minimally invasive pericardial access techniques. A steerable electrophysiology catheter is advanced through the steerable sheath. The transverse pericardial sinus is then accessed, utilizing the maneuvering functions of both the catheter and the sheath while using fluoroscopic imaging— primarily left anterior oblique (LAO) and right anterior oblique (RAO) views.

Once the catheter is in the transverse sinus behind and posterior the great vessels (aorta and pulmonary trunks), the catheter is further advanced close to the right atrioventricular junction on the lateral side. Then, the sheath is advanced over the catheter, while keeping the catheter in position. Once the sheath is in place, the catheter is removed and the angioplasty guidewire is inserted and advanced generously further past the sheath. Then, the lead is advanced over the guidewire inside the sheath using fluoroscopy for guidance through the transverse sinus and close to right atrial (RA) and right ventricle (RV) junctions. With the guidewire and lead in place, the sheath is gradually retracted, making sure the lead stays in the desired position. Once the sheath is completely removed out of the body, the guidewire can be slowly retracted and removed out of the lead, while keeping the lead in the desired position. The lead remains in position over the heart by itself because the inherent positioning-shape features of the lead prevent it from slipping out of the narrower transverse pericardial sinus.

The present invention has been described with reference to several exemplary embodiments thereof. The entire disclosure of any patent or patent application identified herein is hereby fully incorporated by reference for all purposes. The foregoing disclosure has been provided for clarity of understanding by those skilled in the art. No unnecessary limitations should be taken from the foregoing disclosure. It will be apparent to those skilled in the art that changes can be made in the exemplary embodiments described herein without departing from the spirit and scope of the present invention. Thus, the scope of the present invention should not be limited to the exemplary structures and methods described herein, but only by the structures and methods described by the language of the claims and the equivalents of those claimed structures and methods.

What is claimed is:

1. A method of treating a heart, comprising:
providing an elongate lead device including a first zone and a positioning element, the first zone having one or more first zone electrodes;
passing the elongate lead device through a transverse pericardial sinus of the heart, with the one or more first zone electrodes positioned at the transverse pericardial sinus;
interfacing the positioning element with a margin of the transverse pericardial sinus to resist displacement of the elongate lead device; and
stimulating a Bachmann Bundle with a first electrical energy from the one or more first zone electrodes to provide synchronization between a right atrium and a left atrium of the heart.

2. The method of claim 1, wherein the elongate lead device further includes a second zone having one or more second zone electrodes positioned at a second location of the heart and providing a second electrical energy at the second location.

3. The method of claim 2, wherein the second zone is positioned at a first chamber of the heart.

4. The method of claim 3, wherein the one or more second zone electrodes are positioned at a left ventricle of the heart.

5. The method of claim 2, wherein the second zone further includes a plurality of arcuate undulations having the one or more second zone electrodes.

6. The method of claim 5, wherein the second zone further includes at least one secondary transverse curvature extending upwardly transverse to at least one of the plurality of arcuate undulations.

7. The method of claim 2, wherein the elongate lead device further includes a third zone having one or more third zone electrodes adapted for positioning at a third location of the heart and interacting with a third electrical energy at the third location.

8. The method of claim 7, wherein the first zone is adapted for positioning in the transverse pericardial sinus of the heart and the second and third zones are adapted for positioning at one or more chambers of the heart.

9. The method of claim 1, further including providing a defibrillation coil adapted to provide defibrillation therapy to the heart.

10. The method of claim 1, further including providing an implantable device in operative communication with the elongate lead device.

11. The method of claim 1, wherein the first electrical energy includes pacing energy to the heart.

12. The method of claim 1, wherein the positioning element includes a tissue anchoring feature.

13. The method of claim 1, wherein the elongate lead device is constructed at least in part of a shape memory material.

14. The method of claim 1, wherein the elongate lead device includes one or more arcuate portions.

15. The method of claim 1, wherein the positioning element is a resilient positioning element larger than an opening of the transverse pericardial sinus.

16. A method of treating a heart, comprising:
providing an elongate lead device including a first zone, a second zone, and a positioning element, the first zone having two or more first zone electrodes, and the second zone having two or more second zone electrodes provided along outer portions of a plurality of arcuate undulations, with the plurality of arcuate undulations extending away from a longitudinal axis of the elongate lead device;
passing the elongate lead device through a transverse pericardial sinus of the heart;
positioning the first zone at a Bachmann Bundle of the heart;
positioning the second zone at a first chamber of the heart such that the two or more electrodes provided along the outer portions of the plurality of arcuate undulations operatively contact tissue of the first chamber of the heart;
interfacing the positioning element with a margin of the transverse pericardial sinus to resist displacement of the elongate lead device;
providing a first stimulation energy at the Bachmann Bundle; and
providing a second stimulation energy at the first chamber.

17. The method of claim 16, wherein the elongate lead device further includes a third zone having one or more third zone electrodes positionable at a third location of the heart for interacting with a third electrical energy at the third location.

18. The method of 16, further including providing a defibrillation coil adapted to provide defibrillation therapy to the heart.

19. The method of claim 16, further including providing an implantable device in operative communication with the elongate lead device.

20. The method of claim 19, wherein the implantable device is in remote operative communication with the elongate lead device.

21. The method of claim 16, wherein the first chamber of the heart is a right atrium of the heart.

22. The method of claim 16, wherein the first chamber of the heart is a left atrium of the heart.

23. The method of claim 16, wherein the first chamber of the heart is a left ventricle of the heart.

24. The method of claim 16, wherein the first chamber of the heart is a right ventricle of the heart.

25. The method of claim 16, wherein the elongate lead device is constructed at least in part of a shape memory material.

26. The method of claim 25, wherein the elongate lead device is provided in an initial curved parent shape and is deployed in a straightened deployment shape.

27. The method of claim 16, wherein the second zone further includes at least one secondary transverse curvature extending upwardly transverse to at least one of the plurality of arcuate undulations.

28. The method of claim 16, wherein the positioning element is a resilient positioning element larger than an opening of the transverse pericardial sinus.

29. The method of claim 16, wherein the positioning element includes a tissue anchoring feature.

* * * * *